US00PP10191P

United States Patent [19]

Luby et al.

[11] Patent Number: Plant 10,191

[45] Date of Patent: Jan. 13, 1998

[54] STRAWBERRY PLANT CALLED 'MNUS 210'

[75] Inventors: James J. Luby, St. Paul; David K. Wildung, Grand Rapids, both of Minn.; Gene J. Galletta, Laurel, Md.

[73] Assignee: Regents of the University of Minnesota, Minneapolis, Minn.

[21] Appl. No.: 700,297

[22] Filed: Aug. 20, 1996

[51] Int. Cl.[6] ..... A01H 5/00

[52] U.S. Cl. ..... Plt./48

[58] Field of Search ..... Plt./48

[56] References Cited

U.S. PATENT DOCUMENTS

| | | | |
|---|---|---|---|
| P.P. 5,897 | 3/1987 | Sanford et al. | Plt./48 |
| P.P. 8,853 | 8/1994 | Buszard et al. | Plt./48 |
| P.P. 8,991 | 11/1994 | Sanford et al. | Plt./48 |

OTHER PUBLICATIONS

Galleta et al., "Strawberry Cultivar and Selection Red Stele Screening at USDA–Beltsville in 1993–94," *Advances in Strawberry Research*, 13 40–43 (1994).

Luby et al., "Midwest and Plains States Strawberry Cultivars," *Fruit Varieties Journal*, 43 (1) 22–31 (1989).

*Primary Examiner*—James R. Feyrer

*Attorney, Agent, or Firm*—Grace P. Malilay

[57] ABSTRACT

A new and distinct variety of June-bearing strawberry plant named MNUS 210 combines the characteristics of late season fruit ripening, large fruit size, resistance to red stele root rot and common foliar diseases, tolerance to black root rot, and adaptability to various climates typical of the midwestern United States. MNUS 210 yields strawberries characterized by a flavor that is balanced between sweetness and acidity, a glossy appearance with a smooth texture, and a firm flesh.

2 Drawing Sheets

BACKGROUND OF THE INVENTION

MNUS 210 is a June-bearing or short-day strawberry variety (*Fragaria×ananassa*) that is notable for its combination of traits that include a late season of fruit ripening, large fruit size, resistance to five Eastern North American races of *Phytophthora fragariae* Hickman, the causal organism of red stele root rot, tolerance or resistance to several other diseases, and moderate to high productivity in the continental climate of Minnesota with warm summer maximum temperatures of about 40° C., and cold winter minimum temperatures of about –40° C.

BRIEF DESCRIPTION OF THE PHOTOGRAPHS

The accompanying photographs are typical specimens of the plants of the variety and the fruit thereof as depicted in color. The plants and fruit illustrated were grown at the University of Minnesota West Central Experiment Station at Morris, Minn. in July 1995. References to color relate to The Royal Horticultural Society Colour Chart, 1966 edition, noted herein as R.H.S., except for color terms of ordinary dictionary meaning which may occasionally be referred to.

ORIGIN OF THE VARIETY

Figure 1:
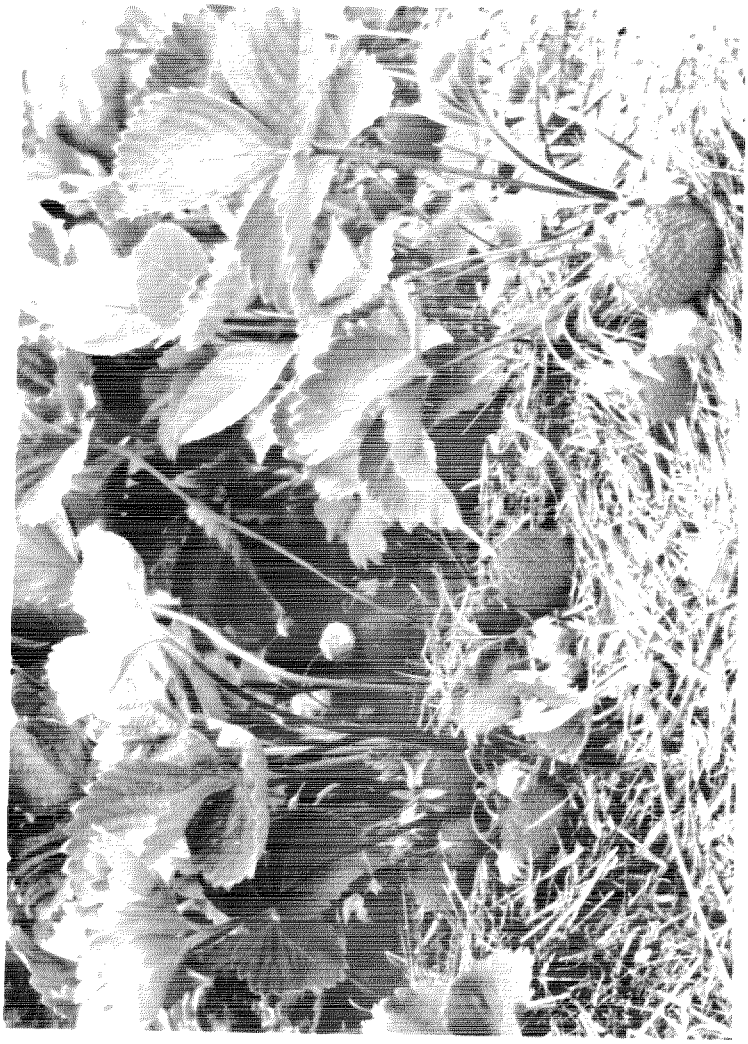
FIG. 1 is a photograph of plants of the variety showing the fruit at different stages of maturity.
Figure 2:
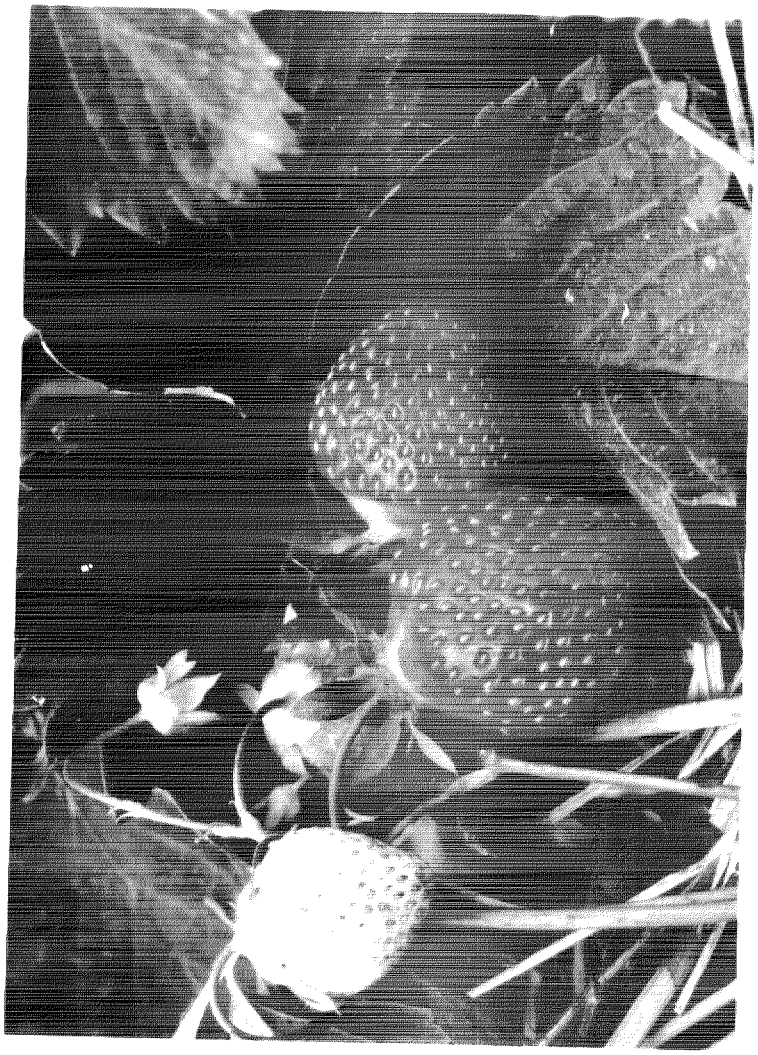
FIG. 2 is a close-up view of fruits of the variety at different stages of maturity. Following is a detailed description or specification of the present variety.

MNUS 210 is a result of a cross between Earliglow×an unnamed seedling designated MNUS 52, made in a controlled breeding program in St. Paul, Minn. MNUS 210 was discovered and selected at Becker, Minn. in 1987. The variety has been stable and uniform through propagation by stolons and by in vitro micropropagation. Off-types, variants and mutations have not been observed. It was propagated by stolons for later observation in trials at the University of Minnesota Horticultural Research Center near Excelsior, Minn. and the North Central Experiment Station at Grand Rapids, Minn. from 1988 to 1990 and at the USDA Beltsville Agricultural Research Center, Beltsville, Md. in 1991.

MNUS 210 was evaluated in replicated yield trials from 1992 through 1995 at the Horticultural Research Center, the North Central Experiment Station, and the West Central Experiment Station at Morris, Minn. (Tables 1 through 8). At each site, plantings were established in 1991 and 1993 and harvested for the two subsequent season. MNUS 210 and other common cultivars of the midwestern United States and Eastern Canada were planted in a randomized complete block design. Plants were spaced 0.45 m apart within rows that were 1.2 m apart and 4 m long. The plants were permitted to form a matted row that was approximately 0.4 m wide. At Grand Rapids, a split plot design was employed on 7 m long plots which were split with half of the plot being mulched for protection during the winter and the other half receiving no mulch. All plots were irrigated, fertilized, and sprayed with fungicide and insecticide as needed in accordance with standard commercial recommendations.

DETAILED DESCRIPTION OF THE VARIETY

Fruit: The fruit of MNUS 210 matures in the latter part of the fruiting season for short day varieties. The fruit matures approximately at the same time as fruit of the cultivars Lateglow, Blomidon and Bounty which are commonly grown in Minnesota (Tables 1, 2, and 3). Compared to these varieties the berries of MNUS 210 has been as large or larger (as measured by average berry weight) in all trials (Tables 1, 2, and 3). Subjective comparisons of the fruit characteristics of MNUS 210 with other adapted varieties are presented in Tables 4, 5, and 6. The flavor is well balanced between sugars and acids and is slightly aromatic. The flesh is firm and the skin is medium to firm. Skin breakdown has been observed in very wet harvest seasons. The berries are strongly glossy and have a scarlet external color corresponding to, plates 45A and 46A of the R.H.S. Colour Chart. The surface of the fruit is smooth to slightly uneven. The flesh is orange red and pink at the center (corresponding to plates 33A and 33B of the R.H.S.

Colour Chart). The shape is blunt-wedge on primary berries to blunt-conic on the secondary and tertiary berries. The berries are equal in length and width to slightly longer than broad. The peduncle is medium in length and prostrate by the time of the first harvest. The calyx is large (equal in diameter to the fruit), showy, generally not inserted in a basin, and partially reflexed, especially on primary berries. Sepals are borne in two whorls with the inner whorl being broad elliptic with sharp points, and the outer whorl being narrow lanceolate with rounded tips. The achenes are yellow and level with or slightly raised from the surface of the fruit.

owers: The inflorescence is usually below the level of the foliage when the flowers are open. The flower size is medium to large. The diameter of the calyx is larger than the diameter of the corolla. The diameter of the inner calyx is similar to the diameter of the outer calyx. Flowers have five petals, and these are generally free and only occasionally touching or overlapping one another on secondary and lower order flowers in an inflorescence. The color of the petal corresponds to plate 155C of the R.H.S. Colour Chart.

lants: Plants of MNUS 210 have large crowns with many petioles and usually form a matted row of medium density. Stolons are thick and green proximal to the mother plant and, distally, take on a medium to strong, red anthocyanin coloration. Pubescence on the stolons is sparse to moderate in density and is appressed.

eaves: The leaves have long petioles giving the appearance of a tall, upright to globose canopy. Pubescence on the petioles is thick and spreading (divaricate). The leaves have three leaflets with weak interveinal blisters and medium pubescence on the adaxial side of the leaflets. Leaflets are equal in size, broadly elliptic, sparsely pubescent, medium green on top, light green on the bottom with prominent veins. The terminal leaflet is equal in length and width to slightly longer in length, has a flat or cupped profile, an obtuse base, and single teeth that are obtuse on younger leaves and rounded on older leaves. Stipules are of medium length and pointed and tan to brown (if dry). The color of the terminal leaflet corresponds to R.H.S. Colour Chart 147A on the upper side and 147B on the lower side.

Fruiting: Results are presented in Tables 1, 2, and 3 from replicated trials conducted at three University of Minnesota experiment station sites in Minnesota: the Horticultural Research Center near Excelsior, the North Central Experiment Station at Grand Rapids, and the West Central Experiment Station at Morris. In all trials, MNUS 210 has consistently had yields similar to or greater than the other late season varieties, Bounty, Blomidon, and Lateglow (Table 1). MNUS 210 has been productive on soils of heavy and light texture in matted row production systems. It has not been trialled in hill systems.

Responses to diseases and stresses: Relative to other cultivars tested in Minnesota, MNUS 210 has moderate to high resistance to the common foliar diseases, powdery mildew (*Sphaerotheca macularis* Walls ex Fr.), leaf scorch (*Diplocarpon earliana* Ell. and Ev.) and leaf spot (*Mycosphaerella fragariae* Tul.) (Tables 7 and 8). MNUS 210 is resistant to five eastern North American races of *Phytophthora fragariae* Hickman (Races A-1, A-2, A-3, A-4 and A-6), the fungus that causes red stele root rot (Table 9). It is also tolerant, relative to other cultivars tested, of black root rot-causing organisms, Rhizoctonia spp. and Pythium spp. based on field observations at the Horticultural Research Center, Excelsior, Minn. (Table 8).

Plants of MNUS 210 have exhibited symptoms of winter injury in some Minnesota trials but has been similar in response compared with other adapted varieties (as indicated by plant stand and vigor ratings in Tables 1, 2 and 3 and subjective ratings in Table 8).

TABLE 1

Performance of strawberry cultivars at the Univ. of Minnesota North Central Experiment Station, Grand Rapids, Minnesota in 1992–1995.[1]

| Cultivar | Mulched | | Unmulched | | Mulched | | Unmulched | |
|---|---|---|---|---|---|---|---|---|
| | Yield (1000 lb/A) | | | | Berry weight (g) | | | |
| | 1992 | 1993 | 1992 | 1993 | 1992 | 1993 | 1992 | 1993 |
| MNUS 210 | 16.0 | 13.7 | 17.2 | 17.0 | 21.3 | 14.8 | 18.5 | 14.3 |
| Blomidon | 7.7 | 7.4 | 5.1 | 8.5 | 13.1 | 10.1 | 12.5 | 9.1 |
| Bounty | 16.4 | 13.9 | 13.8 | 20.5 | 14.8 | 11.9 | 12.1 | 10.8 |
| Lateglow | 9.8 | 7.3 | 11.4 | 9.0 | 19.2 | 15.5 | 16.4 | 12.5 |
| Trumpeter | 16.4 | 14.3 | 12.8 | 13.0 | 13.0 | 11.0 | 13.1 | 10.8 |
| Northland | 16.8 | 19.9 | 14.3 | 20.1 | 14.3 | 11.6 | 13.7 | 10.5 |
| Cavendish | 15.6 | 14.8 | 10.6 | 17.2 | 18.9 | 14.1 | 16.8 | 9.6 |
| Glooscap | 11.0 | 11.9 | 8.0 | 10.0 | 13.7 | 11.6 | 12.1 | 12.0 |
| Kent | 21.4 | 18.5 | 19.0 | 17.9 | 15.7 | 13.1 | 14.2 | 11.8 |
| Honeoye | 12.0 | 11.8 | 12.3 | 13.7 | 16.1 | 13.2 | 14.1 | 10.3 |
| Annapolis | 12.2 | 9.1 | 9.9 | 7.8 | 16.2 | 13.0 | 13.9 | 10.9 |
| Veestar | 6.8 | 8.2 | 7.3 | 7.3 | 11.1 | 6.9 | 9.1 | 6.8 |
| LSD 5% | 3.9 | 4.3 | 4.9 | 5.8 | 2.9 | 1.9 | 2.7 | 2.0 |
| | 1994 | 1995 | 1994 | 1995 | 1994 | 1995 | 1994 | 1995 |
| MNUS 21U | 9.0 | 5.5 | 7.9 | 7.8 | 13.9 | 12.1 | 10.2 | 11.9 |
| Blomidon | 3.0 | 2.1 | 4.3 | 1.5 | 7.9 | 8.2 | 13.4 | 7.8 |
| Lateglow | 4.4 | 3.9 | 4.7 | 3.9 | 14.5 | 9.3 | 12.3 | 9.1 |
| Cavendish | 5.4 | 5.6 | 5.9 | 6.3 | 14.7 | 9.2 | 15.3 | 12.4 |
| Glooscap | 8.2 | 11.4 | 9.5 | 13.7 | 12.0 | 8.5 | 13.2 | 8.6 |
| Jewel | 5.9 | 7.4 | 6.3 | 5.0 | 10.8 | 11.3 | 12.2 | 11.3 |
| Kent | 5.4 | 5.8 | 6.1 | 7.0 | 11.4 | 8.9 | 15.1 | 8.7 |
| Honeoye | 2.6 | 8.3 | 3.1 | 10.0 | 10.6 | 8.4 | 11.5 | 8.0 |
| Seneca | 3.2 | 4.9 | 3.6 | 2.6 | 9.8 | 9.8 | 12.8 | 9.0 |
| Chambly | 1.9 | 7.8 | 1.5 | 5.9 | 10.1 | 7.8 | 14.9 | 8.2 |
| Annapobs | 5.0 | 8.7 | 4.8 | 8.5 | 13.7 | 10.7 | 12.9 | 9.0 |
| Veestar | 6.2 | 9.2 | 6.7 | 7.9 | 8.6 | 6.2 | 9.6 | 7.0 |
| Earliglow | 2.2 | 2.7 | 2.0 | 3.4 | 9.5 | 6.2 | 11.0 | 6.9 |
| LSU 5% | 2.3 | 3.1 | 3.4 | 4.4 | 1.7 | 1.9 | 2.0 | 2.3 |
| | % Early harvest[2] | | | | Stand (%)[3] | | | |
| | 1992 | 1993 | 1992 | 1993 | 1992 | 1993 | 1992 | 1993 |
| MNUS 210 | 4 | 16 | 16 | 41 | 97 | 71 | 99 | 96 |
| Blomidon | 18 | 16 | 36 | 30 | 94 | 75 | 91 | 81 |
| Bounty | 1 | 3 | 14 | 10 | 97 | 99 | 97 | 91 |
| Lateglow | 7 | 9 | 30 | 38 | 94 | 89 | 94 | 93 |
| Trumpeter | 28 | 21 | 61 | 50 | 96 | 96 | 95 | 98 |
| Northland | 25 | 25 | 56 | 50 | 95 | 91 | 93 | 91 |
| Cavendish | 21 | 27 | 54 | 52 | 92 | 81 | 90 | 85 |
| Glooscap | 28 | 27 | 57 | 50 | 86 | 79 | 84 | 88 |
| Kent | 16 | 28 | 46 | 51 | 99 | 98 | 96 | 95 |
| Honeoye | 22 | 36 | 54 | 49 | 93 | 90 | 94 | 76 |
| Annapolis | 57 | 56 | 79 | 76 | 97 | 94 | 97 | 93 |
| Veestar | 58 | 41 | 74 | 59 | 89 | 74 | 92 | 99 |
| LSU 5% | 11 | 12 | 17 | 16 | 10 | 26 | 17 | 23 |
| | 1994 | 1995 | 1994 | 1995 | 1994 | 1995 | 1994 | 1995 |
| MNUS 210 | 3 | 9 | 13 | 16 | 90 | 93 | 100 | 80 |
| Blomidon | 3 | 28 | 21 | 50 | 80 | 57 | 78 | 50 |
| Lateglow | 15 | 13 | 75 | 25 | 80 | 88 | 75 | 80 |
| Cavendish | 36 | 31 | 50 | 40 | 74 | 60 | 80 | 80 |
| Glooscap | 20 | 38 | 32 | 37 | 84 | 80 | 89 | 92 |
| Jewel | 15 | 35 | 30 | 51 | 93 | 85 | 84 | 77 |
| Kent | 31 | 39 | 48 | 46 | 86 | 65 | 61 | 48 |
| Honeoye | 56 | 58 | 68 | 67 | 64 | 88 | 61 | 88 |
| Seneca | 30 | 32 | 42 | 62 | 69 | 67 | 76 | 70 |
| Chambly | 40 | 62 | 75 | 71 | 48 | 87 | 85 | 70 |
| Annapobs | 57 | 61 | 84 | 76 | 85 | 90 | 85 | 90 |

TABLE 1-continued

Performance of strawberry cultivars at the Univ. of Minnesota North Central Experiment Station, Grand Rapids, Minnesota in 1992–1995.[1]

| Cultivar | Mulched | | Unmulched | | Mulched | | Unmulched | |
|---|---|---|---|---|---|---|---|---|
| Veestar | 75 | 70 | 78 | 80 | 88 | 93 | 90 | 95 |
| Earliglow | 49 | 53 | 49 | 70 | 74 | 85 | 49 | 85 |
| LSU 5% | 14 | 16 | 14 | 13 | 20 | 26 | 22 | 29 |

[1]Plantings established in 1991 and 1993 and harvested in the subsequent two years.
[2]% Early harvest = % of total crop harvested from 7/02/92 to 7/13/92 (full season 7/02/92 to 8/05/92); 7/02/93 to 7/12/93 (full season 7/02/93 to 8/02/93); 6/23/94 to 7/1/94 (full season 6/23/94 to 7/22/94); and 6/26/95 to 6/29/95 (full season 6/26/95 to 7/21/95).
[3]% Stand was evaluated during June of each year.
[4]Vigor was rated on a scale of 1 to 9 with 9 being very vigorous.
[5]Winter stand loss was the difference between % Stand in June and % Stand in October of the previous year.

TABLE 2

Performance of strawberry cultivars at the West Central Experiment Station, Morris, Minnesota, in 1992–1995[1].

| Cultivar | Yield (1000 lb/A) | | Berry weight (g) | | % Early harvest[2] | |
|---|---|---|---|---|---|---|
| | 1992 | 1993 | 1992 | 1993 | 1992 | 1993 |
| MNUS 210 | 12.0 | 10.5 | 17.4 | 15.0 | 13 | 3 |
| Blomidon | 9.9 | 7.9 | 11.1 | 12.6 | 3 | 4 |
| Bounty | 6.1 | 4.7 | 11.8 | 8.5 | 2 | 5 |
| Lateglow | 12.0 | 8.0 | 16.0 | 11.2 | 0 | 1 |
| Trumpeter | 7.6 | 9.2 | 13.4 | 9.5 | 5 | 15 |
| Cavendish | 9.0 | 9.1 | 12.6 | 15.9 | 31 | 19 |
| Glooscap | 4.9 | 6.4 | 9.4 | 9.5 | 30 | 22 |
| Jewel | 5.5 | 3.8 | 10.0 | 11.2 | 26 | 37 |
| Kent | 10.5 | 11.7 | 12.4 | 13.9 | 26 | 27 |
| Honeoye | 5.5 | 8.9 | 15.4 | 12.4 | 18 | 24 |
| Redcoat | 12.9 | 9.3 | 9.5 | 10.7 | 26 | 31 |
| Annapolis | 6.8 | 4.7 | 10.0 | 10.4 | 49 | 46 |
| Veestar | 3.3 | 3.7 | 6.4 | 8.2 | 61 | 65 |
| LSD 5% | 3.7 | 3.0 | 3.5 | 1.5 | 12 | 10 |
| | 1994 | 1995 | 1994 | 1995 | 1994 | 1995 |
| MNUS 210 | 5.6 | 6.3 | 9.6 | 8.2 | 0 | 18 |
| Blomidon | 6.7 | 8.3 | 9.2 | 10.5 | 4 | 6 |
| Lateglow | 6.1 | 4.6 | 7.4 | 8.5 | 0 | 18 |
| Cavendish | 19.6 | 15.4 | 12.5 | 13.7 | 18 | 17 |
| Glooscap | 13.9 | 15.4 | 10.2 | 9.1 | 10 | 42 |
| Jewel | 14.3 | 11.9 | 12.3 | 11.7 | 4 | 17 |
| Kent | 17.0 | 11.7 | 10.0 | 9.4 | 23 | 29 |
| Honeoye | 15.1 | 10.7 | 10.6 | 9.3 | 25 | 53 |
| Seneca | 11.7 | 10.3 | 11.7 | 10.4 | 12 | 25 |
| Chambly | 9.6 | 6.2 | 8.3 | 7.1 | 20 | 42 |
| Annapolis | 11.5 | 7.8 | 9.3 | 9.4 | 37 | 61 |
| Veestar | 14.5 | 9.6 | 6.9 | 7.4 | 54 | 75 |
| Earliglow | 8.2 | 3.8 | 6.3 | 6.3 | 44 | 72 |
| LSD 5% | 3.6 | 4.4 | 1.6 | 1.6 | 11 | 14 |

| Cultivar | % Stand[3] | | Vigor[4] | | Winter stand loss (%)[5] | |
|---|---|---|---|---|---|---|
| | 1992 | 1993 | 1992 | 1993 | 1992 | 1993 |
| MNUS 210 | 70 | 68 | 7.8 | 7.8 | n.a. | −5 |
| Blomidon | 85 | 73 | 8.5 | 7.5 | n.a. | −10 |
| Bounty | 83 | 80 | 8.8 | 7.2 | n.a. | −15 |
| Lateglow | 88 | 85 | 8.5 | 8.2 | n.a. | −5 |
| Trumpeter | 88 | 83 | 8.5 | 8.2 | n.a. | −12 |
| Cavendish | 80 | 75 | 7.8 | 7.5 | n.a. | −5 |
| Glooscap | 70 | 58 | 6.8 | 6.2 | n.a. | −15 |
| Jewel | 75 | 63 | 8.0 | 7.2 | n.a. | −18 |
| Kent | 78 | 70 | 8.8 | 6.8 | n.a. | 0 |
| Honeoye | 88 | 83 | 8.8 | 8.8 | n.a. | −13 |

TABLE 2-continued

Performance of strawberry cultivars at the West Central Experiment Station, Morris, Minnesota, in 1992–1995[1].

| | | | | | | |
|---|---|---|---|---|---|---|
| Redcoat | 88 | 93 | 8.8 | 7.5 | n.a. | −5 |
| Annapolis | 80 | 73 | 7.8 | 7.0 | n.a. | −8 |
| Veestar | 80 | 73 | 7.5 | 7.5 | n.a. | −8 |
| LSD 5% | 16 | 21 | 1.2 | 1.6 | n.a. | 12 |
| | 1994 | 1995 | 1994 | 1995 | 1994 | 1995 |
| MNUS 210 | 93 | 25 | 7.5 | 6.0 | −8 | −18 |
| Blomidon | 93 | 78 | 7.8 | 7.3 | −8 | −5 |
| Lateglow | 88 | 63 | 7.0 | 6.8 | −13 | 3 |
| Cavendish | 95 | 83 | 8.5 | 8.3 | 3 | −3 |
| Glooscap | 85 | 85 | 8.0 | 8.0 | −5 | 5 |
| Jewel | 98 | 73 | 9.0 | 8.3 | 0 | 0 |
| Kent | 80 | 55 | 7.5 | 7.3 | −8 | −3 |
| Honeoye | 88 | 70 | 7.8 | 7.8 | 0 | 3 |
| Seneca | 80 | 63 | 8.3 | 8.0 | −13 | −5 |
| Chambly | 80 | 48 | 7.3 | 6.3 | −13 | −8 |
| Annapolis | 83 | 65 | 8.0 | 7.5 | −10 | 0 |
| Veestar | 98 | 88 | 9.0 | 8.3 | 0 | 5 |
| Earliglow | 85 | 70 | 8.3 | 8.0 | −15 | 0 |
| LSD 5% | 13 | 23 | 1.3 | 2.1 | 12 | 8 |

[1]Plantings established in 1991 and 1993 and harvested in the subsequent two years.
[2]% Early harvest = % of total crop harvested from 06/15/92 to 06/24/92 (full season 06/15/92 to 07/15/92); 06/21/93 to 06/28/93 (full season 06/21/93 to 07/19/93); 06/08/94 to 06/15/94 (full season 06/08/94 to 07/05/94); and 06/19/95 to 06/23/95 (full season 06/19/95 to 07/06/95).
[3]% Stand was evaluated during June of each year.
[4]Vigor was rated on a scale of 1 to 9 with 9 being very vigorous.
[5]Winter stand loss was the difference between % Stand in June and % Stand in October of the previous year.

TABLE 3

Performance of strawberry cultivars at the University of Minnesota Horticultural Research Center, Excelsior, Minnesota in 1992, 1994, and 1995.[1]

| | Yield (1000 lb/A) | | | Berry weight (g) | | |
|---|---|---|---|---|---|---|
| Cultivar | 1992 | 1994 | 1995 | 1992 | 1994 | 1995 |
| MNUS 210 | 5.8 | 11.7 | 14.7 | 17.5 | 14.0 | 13.2 |
| Blomdon | 6.6 | 7.3 | 6.7 | 11.8 | 9.5 | 10.2 |
| Bounty | 6.5 | n.a. | n.a. | 10.0 | n.a. | n.a. |
| Lateglow | 6.5 | 9.3 | 9.0 | 14.4 | 11.5 | 11.2 |
| Cavendish | 5.5 | 15.4 | 16.2 | 15.0 | 12.2 | 10.5 |
| Glooscap | 4.6 | 13.1 | 14.0 | 10.6 | 10.0 | 7.3 |
| Jewel | 5.2 | 12.7 | 12.1 | 12.9 | 12.8 | 10.8 |
| Kent | 8.1 | 14.2 | 10.8 | 16.3 | 9.6 | 8.6 |
| Honeoye | 12.9 | 10.4 | 9.5 | 14.1 | 9.1 | 7.5 |
| Seneca | n.a. | 10.7 | 9.8 | n.a. | 11.9 | 9.8 |
| Startyme | n.a. | 8.6 | 6.5 | n.a. | 12.0 | 11.8 |
| Chambly | n.a. | 8.5 | 13.2 | n.a. | 9.3 | 7.9 |
| Redcoat | 8.7 | n.a. | n.a. | 11.2 | n.a. | n.a. |
| Annapolis | 7.1 | 8.8 | 10.2 | 17.4 | 14.8 | 8.9 |
| Veestar | 9.1 | 10.4 | 9.9 | 7.5 | 9.1 | 8.0 |
| Earliglow | n.a. | 6.5 | 9.5 | n.a. | 9.7 | 9.1 |
| LSD 5% | 3.3 | 3.5 | 2.7 | 3.1 | 1.3 | 1.1 |

| | % Early harvest[2] | | | Stand (%)[3] | | |
|---|---|---|---|---|---|---|
| Cultivar | 1992 | 1994 | 1995 | 1992 | 1994 | 1995 |
| MNUS 210 | 52 | 4 | 22 | 68 | 68 | 83 |
| Blomdon | 37 | 15 | 22 | 68 | 60 | 68 |
| Bounty | 18 | n.a. | n.a. | 75 | n.a. | n.a. |
| Lateglow | 35 | 3 | 0 | 75 | 70 | 83 |
| Cavendish | 52 | 27 | 20 | 63 | 55 | 75 |
| Glooscap | 60 | 15 | 34 | 58 | 70 | 85 |
| Jewel | 79 | 26 | 25 | 58 | 68 | 73 |
| Kent | 63 | 29 | 47 | 65 | 68 | 73 |
| Honeoye | 64 | 51 | 67 | 83 | 65 | 65 |
| Seneca | n.a. | 32 | 47 | n.a. | 70 | 65 |

TABLE 3-continued

Performance of strawberry cultivars at the University of Minnesota Horticultural Research Center, Excelsior, Minnesota in 1992, 1994, and 1995.[1]

| | | | | | | |
|---|---|---|---|---|---|---|
| tyme | n.a. | 15 | 24 | n.a. | 60 | 70 |
| ımbly | n.a. | 36 | 55 | n.a. | 63 | 73 |
| icoat | 71 | n.a. | n.a. | 75 | n.a. | n.a. |
| ıapolis | 94 | 57 | 49 | 80 | 65 | 73 |
| star | 58 | 61 | 69 | 78 | 80 | 90 |
| liglow | n.a. | 66 | 55 | n.a. | 65 | 78 |
| ) 5% | 22 | 14 | 12 | 18 | 18 | 11 |

| | Vigor[4] | | |
|---|---|---|---|
| Cultivar | 1992 | 1994 | 1995 |
| MNUS 210 | 7.5 | 7.0 | 8.0 |
| Blomdon | 7.3 | 6.3 | 6.8 |
| Bounty | 7.8 | n.a. | n.a. |
| Lateglow | 7.8 | 7.0 | 8.0 |
| Cavendish | 7.0 | 7.0 | 8.0 |
| Glooscap | 8.5 | 7.3 | 7.3 |
| Jewel | 6.8 | 8.0 | 8.0 |
| Kent | 8.0 | 6.3 | 7.0 |
| Honeoye | 8.3 | 6.5 | 5.8 |
| Seneca | n.a. | 6.8 | 7.3 |
| Startyme | n.a. | 7.0 | 7.5 |
| Chambly | n.a. | 7.3 | 7.5 |
| Redcoat | 8.0 | n.a. | n.a. |
| Annapolis | 8.0 | 6.8 | 7.3 |
| Veestar | 7.0 | 7.3 | 8.3 |
| Earliglow | n.a. | 7.5 | 8.8 |
| LSD 5% | 1.1 | 1.1 | 1.0 |

ıntings established in 1991 and 1993 and harvested in the subsequent one wo years, respectively.
Early harvest = % of total crop harvested from 6/11/92 to 6/16/92 (full ıon 6/11/92 to 7/02/92); 6/14/94 to 6/17/1/94 (full season 6/14/94 to 5/94); and 6/16/95 to 6/23/95 (full season 6/16/95 to 7/06/95).
Stand was evaluated during June of each year.
gor was rated on a scale of 1 to 9 with 9 being very vigorous.

TABLE 4

Fruit quality ratings of strawberry cultivars at the North Central ɔeriment Station, Grand Rapids, Minnesota in trials from 1992–1995.[1]

| tivar | Appearance[2] | | Skin color[2] | | Flesh color[2] | |
|---|---|---|---|---|---|---|
| | 1992 | 1993 | 1992 | 1993 | 1992 | 1993 |
| IUS 210 | 7.5 | 7.7 | 7.0 | 7.7 | 8.0 | 7.7 |
| mıdon | 7.5 | 7.3 | 8.0 | 7.3 | 8.5 | 7.8 |
| ınty | 7.0 | 8.0 | 6.5 | 8.2 | 8.0 | 6.2 |
| eglow | 8.0 | 7.7 | 7.5 | 7.5 | 7.0 | 8.0 |
| thland | 7.0 | 7.7 | 7.0 | 7.7 | 8.0 | 8.3 |
| mpeter | 7.5 | 7.7 | 8.0 | 8.0 | 8.5 | 8.3 |
| endish | 7.5 | 7.7 | 8.0 | 8.0 | 8.0 | 7.8 |
| oscap | 8.0 | 8.3 | 8.5 | 8.5 | 8.5 | 8.3 |
| ıt | 8.0 | 8.0 | 8.0 | 8.2 | 8.0 | 8.0 |
| ıeoye | 7.0 | 7.7 | 7.0 | 8.0 | 7.5 | 8.0 |
| ıapolis | 7.5 | 7.8 | 8.0 | 8.0 | 8.0 | 7.7 |
| star | 6.5 | 5.3 | 7.5 | 6.3 | 8.0 | 8.0 |
| | 1994 | 1995 | 1994 | 1995 | 1994 | 1995 |
| IUS 210 | 6.5 | 7.0 | 7.0 | 7.0 | 7.0 | 7.0 |
| ımidon | 7.5 | 5.5 | 8.5 | 6.5 | 8.0 | 8.0 |
| eglow | 8.0 | 7.0 | 6.5 | 7.0 | 8.0 | 8.7 |
| endish | 7.5 | 6.0 | 8.5 | 7.5 | 8.0 | 8.5 |
| oscap | 8.0 | 7.8 | 8.0 | 8.0 | 8.5 | 8.5 |
| el | 8.0 | 7.3 | 8.0 | 7.7 | 8.0 | 7.7 |
| ıt | 8.0 | 6.7 | 8.0 | 7.3 | 8.0 | 6.3 |
| nooye | 8.0 | 7.5 | 8.0 | 8.0 | 8.0 | 8.0 |
| ıeca | 6.0 | 7.0 | 7.5 | 7.5 | 8.0 | 7.5 |
| ambly | 8.0 | 6.5 | 8.0 | 7.0 | 8.0 | 7.5 |
| napolis | 7.0 | 6.5 | 6.0 | 6.5 | 7.0 | 7.5 |

TABLE 4-continued

Fruit quality ratings of strawberry cultivars at the North Central Experiment Station, Grand Rapids, Minnesota in trials from 1992–1995.[1]

| | | | | | | |
|---|---|---|---|---|---|---|
| Veestar | 6.5 | 6.0 | 6.5 | 7.8 | 7.5 | 7.3 |
| Earliglow | 7.0 | 7.0 | 8.0 | 7.0 | 8.0 | 8.0 |

| Cultivar | Firmness[2] | | Flavor[2] | | Overall fruit quality[3] | |
|---|---|---|---|---|---|---|
| | 1992 | 1993 | 1992 | 1993 | 1992 | 1993 |
| MNUS 210 | 8.0 | 7.7 | 7.5 | 7.3 | 7.5 | 7.5 |
| Blomidon | 8.0 | 6.3 | 6.5 | 6.3 | 6.5 | 6.5 |
| Bounty | 6.0 | 6.2 | 7.0 | 6.7 | 6.5 | 7.5 |
| Lateglow | 8.0 | 7.5 | 7.5 | 7.5 | 8.0 | 7.7 |
| Northland | 5.0 | 5.3 | 6.5 | 6.3 | 7.0 | 6.7 |
| Trumpeter | 6.0 | 5.3 | 7.0 | 5.7 | 7.0 | 6.3 |
| Cavendish | 7.0 | 7.5 | 7.5 | 7.0 | 8.0 | 8.0 |
| Glooscap | 7.0 | 6.8 | 7.0 | 7.5 | 7.5 | 7.7 |
| Kent | 6.5 | 7.2 | 7.0 | 6.7 | 8.0 | 8.2 |
| Honeoye | 6.5 | 6.7 | 6.5 | 6.0 | 7.0 | 6.8 |
| Annapolis | 7.0 | 7.5 | 7.5 | 7.0 | 7.5 | 6.2 |
| Veestar | 6.0 | 5.7 | 6.5 | 5.7 | 6.0 | 5.3 |
| | 1994 | 1995 | 1994 | 1995 | 1994 | 1995 |
| MNUS 210 | 7.0 | 7.5 | 6.0 | 7.5 | — | 8.0 |
| Blomidon | 7.0 | 8.0 | 5.0 | 6.5 | — | 5.5 |
| Lateglow | 7.0 | 7.0 | 7.0 | 7.0 | 8.0 | 7.0 |
| Cavendish | 7.5 | 6.3 | 7.5 | 8.0 | 8.0 | 7.0 |
| Glooscap | 7.0 | 7.0 | 6.5 | 7.5 | 8.0 | 8.0 |
| Jewel | 7.0 | 7.0 | 7.5 | 7.0 | 7.5 | 6.7 |
| Kent | 6.5 | 6.7 | 6.0 | 6.7 | 7.5 | 6.7 |
| Honooye | 6.5 | 6.7 | 7.0 | 6.8 | 7.0 | 7.0 |
| Seneca | 7.5 | 8.0 | 6.5 | 6.5 | 6.5 | 6.5 |
| Chambly | 7.0 | 7.0 | 6.5 | 5.5 | 6.5 | 6.0 |
| Annapolis | 7.0 | 6.5 | 7.0 | 7.0 | 7.0 | 6.5 |
| Veestar | 5.5 | 6.0 | 6.0 | 6.0 | 6.0 | 6.0 |
| Earliglow | 7.0 | 7.5 | 7.5 | 6.5 | 7.0 | 6.5 |

[1]Plantings were established in 1991 and 1993 and evaluated for the subsequent two years.
[2]Appearance, Skin color, Flesh color, Firmness, and Flavor are rated on a scale of 1 to 9 with 9 being excellent or very pleasing in appearance, color, or flavor, and very firm flesh in response to thumb pressure.
[3]Overall fruit quality is rated on a scale of 1 to 9 with 9 being best or most desirable.

TABLE 5

Fruit quality ratings of strawberry cultivars at the West Central Experiment Station, Morris, Minnesota in 1992–1995.[1]

| Cultivar | Appearance[2] | | Firmness[2] | | Skin toughness[2] | |
|---|---|---|---|---|---|---|
| | 1992 | 1993 | 1992 | 1993 | 1992 | 1993 |
| MNUS 210 | 8.0 | 8.0 | 9.0 | 8.0 | 7.0 | 8.0 |
| Blomidon | 8.0 | 9.0 | 7.0 | 8.0 | 7.0 | 8.0 |
| Bounty | 7.0 | 7.0 | 6.0 | 7.0 | 7.0 | 7.0 |
| Lateglow | 8.0 | 8.0 | 8.0 | 7.0 | 6.0 | 7.0 |
| Trumpeter | 6.0 | 7.0 | 6.0 | 6.0 | 5.0 | 5.0 |
| Cavendish | 6.0 | 7.0 | 8.0 | 8.0 | 6.0 | 6.0 |
| Glooscap | 8.0 | 8.0 | 7.0 | 7.0 | 7.0 | 6.0 |
| Jewel | — | 7.0 | — | 7.0 | — | 8.0 |
| Kent | 7.0 | 8.0 | 7.0 | 7.0 | 6.0 | 7.0 |
| Honeoye | 7.0 | 8.0 | 7.0 | 7.0 | 8.0 | 6.0 |
| Redcoat | 6.0 | 7.0 | 6.0 | 6.0 | 7.0 | 6.0 |
| Annapolis | 8.0 | 7.0 | 8.0 | 8.0 | 8.0 | 7.0 |
| Veestar | 7.0 | 7.0 | 6.0 | 6.0 | 7.0 | 6.0 |
| | 1994 | 1995 | 1994 | 1995 | 1994 | 1995 |
| MNUS 210 | 7.0 | 7.5 | 8.0 | 8.0 | 8.0 | 8.0 |
| Blomidon | 7.5 | 8.0 | 8.0 | 7.5 | 8.0 | 7.0 |
| Lateglow | 7.0 | 7.0 | 6.0 | 7.0 | 6.0 | 7.5 |
| Cavendish | 7.5 | 6.5 | 7.0 | 7.5 | 7.0 | 7.5 |
| Glooscap | 7.5 | 6.0 | 7.0 | 7.0 | 6.0 | 7.0 |
| Jewel | 8.0 | 8.0 | 7.0 | 8.0 | 7.0 | 8.0 |

TABLE 5-continued

Fruit quality ratings of strawberry cultivars at the West Central Experiment Station, Morris, Minnesota in 1992–1995.[1]

| | | | | | | |
|---|---|---|---|---|---|---|
| Kent | 7.5 | 7.0 | 7.0 | 7.0 | 6.0 | 7.0 |
| Honeoye | 6.5 | 6.0 | 6.0 | 7.0 | 6.0 | 6.0 |
| Seneca | 8.0 | 8.0 | 8.0 | 8.0 | 7.0 | 7.0 |
| Chambly | 7.0 | 6.0 | 7.0 | 7.0 | 7.0 | 8.0 |
| Annapolis | 8.0 | 7.0 | 7.0 | 8.0 | 7.0 | 7.0 |
| Veestar | 6.5 | 5.0 | 6.0 | 5.0 | 5.0 | 5.0 |
| Earliglow | 6.5 | 7.0 | 7.0 | 7.5 | 6.0 | 7.0 |

| Cultivar | Flavor[2] | | Overall fruit quality[3] | |
|---|---|---|---|---|
| | 1992 | 1993 | 1992 | 1993 |
| MNUS 210 | 7.0 | 8.0 | 3.5 | 4.0 |
| Blomidon | 7.0 | 7.0 | 3.0 | 4.0 |
| Bounty | 8.0 | 7.0 | 2.5 | 2.5 |
| Lateglow | 7.0 | 7.5 | 3.0 | 3.5 |
| Trumpeter | 7.0 | 6.0 | 2.0 | 2.0 |
| Cavendish | 7.0 | 7.0 | 3.0 | 2.0 |
| Glooscap | 7.0 | 7.0 | 2.5 | 2.5 |
| Jewel | — | 8.0 | — | 3.0 |
| Kent | 6.0 | 6.0 | 2.0 | 3.5 |
| Honeoye | 6.0 | 6.0 | 2.5 | 3.0 |
| Redcoat | 7.0 | 6.0 | 2.0 | 2.5 |
| Annapolis | 7.0 | 7.5 | 3.0 | 3.5 |
| Veestar | 7.0 | 7.0 | 2.0 | 2.0 |
| | 1994 | 1995 | 1994 | 1995 |
| MNUS 210 | 7.0 | 8.0 | 2.5 | 3 5 |
| Blomidon | 7.5 | 7.0 | 3.5 | 3.0 |
| Lateglaw | 7.0 | 7.0 | 2.5 | 2.5 |
| Cavendish | 7.5 | 7.0 | 3.5 | 3.0 |
| Glooscap | 7.0 | 7.0 | 3.0 | 2.5 |
| Jewel | 6.5 | 7.5 | 3.0 | 3.5 |
| Kent | 7.0 | 7.5 | 3.0 | 2.5 |
| Honeoye | 7.0 | 7.0 | 2.0 | 2.0 |
| Seneca | 7.5 | 7.0 | 3.5 | 3.5 |
| Chambly | 6.0 | 6.5 | 2.5 | 2.5 |
| Annapolis | 7.0 | 7.5 | 3.5 | 3.0 |
| Veestar | 7.0 | 8.0 | 2.0 | 2.0 |
| Earliglow | 6.0 | 8.0 | 2.0 | 3.0 |

[1]Plantings established in 1991 and 1993 and evaluated in the subsequent two years.
[2]Appearance, Firmness, Skin toughness, and Flavor are rated on a scale of 1 to 9 with 9 being excellent or very pleasing in appearance or flavor, and very firm flesh or tough skin in response to thumb pressure.
[3]Overall fruit quality is rated on a scale of 1 to 5 with 5 being best or most desirable.

TABLE 6

Fruit quality ratings of strawberry cultivers at the University of Minnesota Horticultural Research Center, Excelsior, Minnesota in 1992 and 1994.[1]

| | Appearance[2] | | Firmness[2] | | Skin toughness[2] | |
|---|---|---|---|---|---|---|
| Cultivar | 1992 | 1994 | 1992 | 1994 | 1992 | 1994 |
| MNUS 210 | 7.0 | 8.0 | 8.0 | 8.0 | 8.0 | 8.0 |
| Blomidon | 8.5 | 8.0 | 8.0 | 7.0 | 8.0 | 7.0 |
| Bounty | 6.5 | n.a. | 8.0 | n.a. | 5.0 | n.a. |
| Lateglow | 7.5 | 6.0 | 7.0 | 8.0 | 8.0 | 7.0 |
| Cavendish | 7.5 | 8.0 | 8.0 | 7.0 | 6.0 | 7.0 |
| Chambly | n.a. | 7.0 | n.a. | 7.0 | n.a. | 7.0 |
| Glooscap | 7.5 | 6.0 | 6.0 | 7.0 | 6.0 | 7.0 |
| Jewel | 9.0 | 8.0 | 8.0 | 7.0 | 7.0 | 8.0 |
| Kent | 8.5 | 8.0 | 8.0 | 7.0 | 7.0 | 6.0 |
| Honeoye | 8.0 | 7.0 | 6.0 | 7.0 | 6.0 | 6.0 |
| Seneca | n.a. | 8.0 | n.a. | 8.0 | n.a. | 7.0 |
| Startyme | n.a. | 7.0 | n.a. | 8.0 | n.a. | 8.0 |
| Redcoat | 8.0 | n.a. | 6.0 | n.a. | 6.0 | n.a. |
| Annapolis | 9.0 | 8.0 | 8.0 | 7.0 | 7.0 | 8.0 |

TABLE 6-continued

Fruit quality ratings of strawberry cultivers at the University of Minnesota Horticultural Research Center, Excelsior, Minnesota in 1992 and 1994.[1]

| | | | | | | |
|---|---|---|---|---|---|---|
| Veestar | 8.5 | 7.0 | 4.0 | 6.0 | 5.0 | 6.0 |
| Earliglow | n.a. | 8.0 | n.a. | 7.0 | n.a. | 7.0 |

| Cultivar | Flavor[2] | | Overall fruit quality[2] | |
|---|---|---|---|---|
| | 1992 | 1994 | 1992 | 1994 |
| MNUS 210 | 7.0 | 8.0 | 3.0 | 3.0 |
| Blomidon | 7.0 | 7.0 | 4.0 | 3.0 |
| Bounty | 7.0 | n.a. | 2.0 | n.a. |
| Lateglow | 8.0 | 7.0 | 4.0 | 2.5 |
| Cavendish | 8.0 | 7.0 | 4.0 | 3.0 |
| Chambly | n.a. | 7.0 | n.a. | 2.5 |
| Glooscap | 7.0 | 7.0 | 3.0 | 3.0 |
| Jewel | 7.0 | 7.0 | 4.0 | 4.0 |
| Kent | 7.0 | 7.0 | 4.0 | 3.0 |
| Honeoye | 7.0 | 7.0 | 3.0 | 2.5 |
| Seneca | n.a. | 7.0 | n.a. | 3.0 |
| Startyme | n.a. | 9.0 | n.a. | 3.5 |
| Redcoat | 6.0 | n.a. | 2.0 | n.a. |
| Annapolis | 7.0 | 7.0 | 4.0 | 3.5 |
| Veestar | 7.0 | 7.0 | 1.0 | 2.0 |
| Earliglow | n.a. | 8.0 | n.a. | 3.0 |

[1]Plantings established in 1991 and 1993 were evaluated in 1992 and 1994, respectively.
[2]Appearance, Firmness, Skin toughness, and Flavor are rated on a scale of 1 to 9 with 9 being excellent or very pleasing in appearance or flavor, and very firm flesh or tough skin in response to thumb pressure.
[3]Overall fruit quality is rated on a scale of 1 to 5 with 5 being best or most desirable.

TABLE 7

Disease responses of strawberry cultivars at the University of Minnesota North Central Experiment Station, Grand Rapids, Minnesota in 1992 and 1993.[1,2]

| Cultivar | Leat spot | | Powdery mildew | |
|---|---|---|---|---|
| | 1992 | 1993 | 1992 | 1993 |
| MNUS 210 | 7.0 | 7.2 | 7.5 | 7.2 |
| Blomidon | 7.0 | 7.2 | 7.5 | 6.7 |
| Bounty | 6.5 | 6.2 | 7.2 | 7.2 |
| Lateglow | 4.5 | 4.7 | 5.2 | 4.5 |
| Northland | 6.2 | 6.5 | 4.7 | 4.7 |
| Trumpeter | 7.2 | 7.0 | 4.7 | 4.7 |
| Cavendish | 7.0 | 7.0 | 5.5 | 5.7 |
| Glooscap | 7.0 | 7.5 | 7.0 | 6.2 |
| Kent | 5.5 | 6.0 | 8.0 | 7.2 |
| Honeoye | 6.2 | 6.7 | 6.2 | 6.0 |
| Annapolis | 7.0 | 7.2 | 5.7 | 5.7 |
| Veestar | 7.2 | 7.0 | 5.5 | 5.5 |
| LSD 5% | 1.1 | 0.9 | 0.7 | 0.8 |
| | 1994 | 1995 | 1994 | 1995 |
| MNUS 210 | 7.8 | 7.0 | 7.5 | 7.7 |
| Blomidon | 7.5 | 7.7 | 7.0 | 8.0 |
| Lateglow | 5.3 | 3.7 | 5.3 | 4.7 |
| Cavendish | 6.3 | 7.0 | 5.8 | 5.7 |
| Chambly | 7.5 | 6.7 | 5.3 | 5.0 |
| Glooscap | 7.8 | 5.0 | 5.5 | 7.0 |
| Jewel | 6.8 | 6.7 | 7.8 | 7.7 |
| Kent | 4.5 | 5.0 | 7.8 | 7.0 |
| Honeoye | 6.3 | 5.7 | 6.5 | 6.3 |
| Seneca | 7.0 | 5.7 | 7.8 | 7.7 |
| Annapolis | 7.5 | 7.0 | 6.0 | 6.0 |
| Veestar | 7.3 | 6.3 | 5.8 | 6.3 |

TABLE 7-continued

Disease responses of strawberry cultivars at the University of Minnesota North Central Experiment Station, Grand Rapids, Minnesota in 1992 and 1993.[1,2]

| Cultivar | Leat spot | | Powdery mildew | |
|---|---|---|---|---|
| Earliglow | 7.5 | 7.3 | 5.8 | 5.7 |
| LSD 5% | 0.9 | 1.2 | 0.8 | 0.7 |

ntings established in 1991 and 1993 and observed for the subsequent 2 's.

af spot and powdery mildew ratings are on a scale from 1 = very severe ction to 9 = no infection.

TABLE 8

Disease responses of strawberry cultivars at the University of Minnesota Horticultural Research Center, Excelsior, Minnesota, in 1994 and 1995.[1,2]

| | Winter injury | Black root rot | Leaf scorch | | Powdery mildew |
|---|---|---|---|---|---|
| tivar | 1994 | 1995 | 1994 | 1995 | 1995 |
| US 210 | 6.5 | 7.5 | 8.0 | 7.3 | 7.0 |
| midon | 7.3 | 5.5 | 8.0 | 7.5 | 8.0 |
| :glow | 7.3 | 7.5 | 7.0 | 6.3 | 6.0 |
| endish | 7.0 | 7.5 | 8.0 | 8.5 | 7.3 |
| oscap | 7.8 | 7.0 | 8.0 | 7.8 | 7.0 |
| el | 6.5 | 6.8 | 8.0 | 7.3 | 7.5 |
| it | 7.0 | 5.3 | 5.0 | 5.5 | 7.8 |
| ieoye | 7.0 | 4.3 | 7.0 | 5.8 | 8.0 |
| eca | 6.8 | 5.8 | 8.0 | 6.5 | 8.0 |
| tyme | 7.0 | 6.5 | 6.0 | 7.0 | 7.0 |
| imbly | 7.5 | 6.5 | 9.0 | 8.0 | 6.5 |
| iapolis | 7.3 | 6.5 | 8.0 | 8.5 | 7.3 |
| star | 7.3 | 8.3 | 8.0 | 8.3 | 7.0 |

TABLE 8-continued

Disease responses of strawberry cultivars at the University of Minnesota Horticultural Research Center, Excelsior, Minnesota, in 1994 and 1995.[1,2]

| | Winter injury | Black root rot | Leaf scorch | | Powdery mildew |
|---|---|---|---|---|---|
| Cultivar | 1994 | 1995 | 1994 | 1995 | 1995 |
| Earliglow | 7.3 | 8.5 | 9.0 | 8.0 | 6.0 |
| LSD 5% | 0.7 | 1.7 | n.a. | 0.8 | 0.7 |

[1]Planting established in 1993.
[2]Winter injury, Black root rot, Leaf scorch, and Powdery mildew were rated on a scale from 1 = very severe infection or damage to 9 = no infection or damage.

TABLE 9

Responses of strawberry genotypes to red stele root rot screening with mix if *Pytophthora tragariae* races A-1, A.2, A-3, A-4, and A-6 by root-dip inoculation at Beltsville, Maryland, 1993–94.[1]

| | Replicatian mean root scores[2] | |
|---|---|---|
| Genotype | Range | Mean |
| MNUS 210 | 8.0–8.5 | 8.2 |
| Yaquina B (resistant standard) | 8.0–8.5 | 8.2 |
| Del Norte (intermediate standard) | 8.0–8.5 | 8.2 |
| Blakemore (Susceptible standard) | 4.5–5.0 | 4.7 |

[1]See G. J. Galleta, Strawbarry Cultivar and Selection Red Stele Screernng at USDA - Beltsville in 1993–94, 13 Advances in Strawberry Research 40 (1994).
[2]Three replications with two-plant plots were scored for root injury with 1–3 being very susceptible, 4–5 being susceptible, 8–7 being tolerant, and 8-9 being resistant. Blakemore was significantly more susceptible than the other varieties at P = 0.05 using Duncan's Multiple Range Test for mean separation.

We claim:

1. A new and distinct variety of strawberry plant, substantially as illustrated and described, characterized by the combined characteristics of its late season of fruit ripening, large size of fruit, resistance to red stele root rot and to the common foliar diseases, tolerance to black root rot, and adaptability to various climates typical of the midwestern United States.

* * * * *